United States Patent [19]

Toyofuku et al.

[11] Patent Number: 4,587,254

[45] Date of Patent: May 6, 1986

[54] 1,3,4-THIADIAZOLE DERIVATIVES, PROCESS FOR THE PRODUCTION THEREOF AND USE THEREOF AS ANTIULCER AGENT

[75] Inventors: Hatsunori Toyofuku, Yokohama; Yoshihiro Tsuriya, Hatano; Toshio Kuroda, Sagamihara; Hitoshi Aoki, Fujisawa; Hiroshi Nagasawa, Hatano, all of Japan

[73] Assignee: Wakamoto Pharmaceutical Co., Ltd., Tokyo, Japan

[21] Appl. No.: 632,333

[22] Filed: Jul. 19, 1984

[30] Foreign Application Priority Data

Sep. 24, 1983 [JP] Japan ................... 58-175221

[51] Int. Cl.$^4$ .................. C07D 31/445; C07D 417/12
[52] U.S. Cl. ........................... 514/326; 546/209; 548/141
[58] Field of Search .............. 546/209; 548/141; 514/326

[56] References Cited

U.S. PATENT DOCUMENTS 2,891,961  6/1959  Turner et al. ................ 548/141

*Primary Examiner*—Robert T. Bond
*Attorney, Agent, or Firm*—Harry M. Weiss & Associates

[57] ABSTRACT

New 1,3,4-thiadiazole derivatives of the general formula (I):

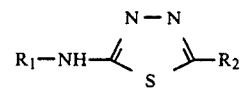

wherein $R_1$ represents a group of the formula:

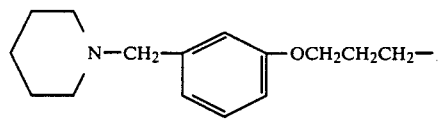

and $R_2$ represents an amino, lower alkylamino, cyclohexylamino, benzoylamino, mercapto or lower alkylthio group, a process for the production of them and the use of the derivatives as antiulcer agents.

12 Claims, No Drawings

1,3,4-THIADIAZOLE DERIVATIVES, PROCESS FOR THE PRODUCTION THEREOF AND USE THEREOF AS ANTIULCER AGENT

BACKGROUND OF THE INVENTION

1. Field of the Invention

The present invention relates to new 1,3,4-thiadiazole derivatives useful as antiulcer agents of the general formula (I):

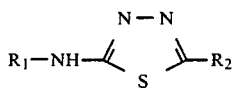

wherein $R_1$ represents a group of the formula:

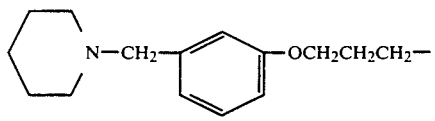

and $R_2$ represents an amino, lower alkylamino, cyclohexylamino, benzoylamino, mercapto or lower alkylthio group and a process for producing the same.

The compounds of the formula (I) are new compounds having an excellent antagonism to histamine $H_2$ receptors and useful as long lasting inhibitors against secretion of acid in the stomach or antiulcer agents.

2. Description of the Prior Art

There have been known numerous compounds antagonistic to histamine $H_2$ receptors such as cimetidine (U.S. Pat. No. 3,950,333) and ranitidine (U.S. Pat. No. 4,128,658). However, they are not always satisfactory, since they have some adverse reactions and their effect of inhibiting the secretion of acid in the stomach is only transient to require an increase of the dose and number of times of the administration.

After synthesis of numerous compounds and intensive investigations made for the purpose of solving these problems, the inventors have succeeded in producing new compounds (I) having quite excellent effect of inhibiting the secretion of acid in the stomach, pepsin-inhibitory effect and antiulcer effect.

SUMMARY OF THE INVENTION

The present invention provides 1,3,4-thiadiazole derivatives of the general formula (I):

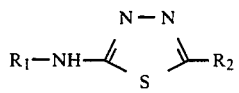

wherein $R_1$ represents a group of the formula:

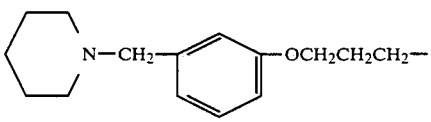

and $R_2$ represents an amino, lower alkylamino, cyclohexylamino, benzoylamino, mercapto or lower alkylthio group and acid-addition salts of them.

The present invention provides also a process for producing 1,3,4-thiadiazole derivatives of the general formula (I):

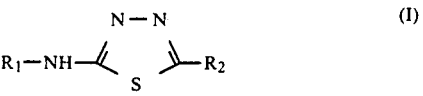

wherein $R_1$ and $R_2$ have the same meaning as above by ring-closing condensation of bithioureas or thiocarbamyl dithiocarbazinic acid esters of the general formula (II):

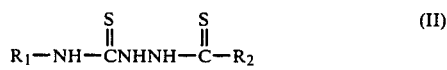

wherein $R_1$ and $R_2$ have the same meaning as above.

Further, the present invention provides an anti-ulcer agent characterized by containing as an active ingredient a 1,3,4-thiadiazole derivative of the general formula (I):

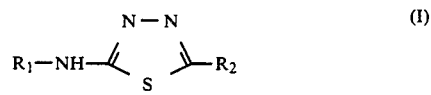

wherein $R_1$ and $R_2$ have the same meaning as above.

DETAILED DESCRIPTION OF THE PREFERRED EMBODIMENTS

The present invention relates to new 1,3,4-thiadiazole derivatives useful as antiulcer agents, process for the production thereof and the use thereof.

The 1,3,4-thiadiazole derivatives have the following general formula:

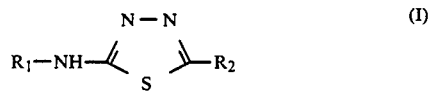

wherein $R_1$ represents a group of the formula:

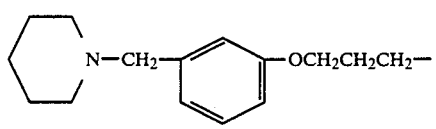

and $R_2$ represents an amino, lower alkylamino, cyclohexylamino, benzoylamino, mercapto or lower alkylthio group.

The lower alkylamino and lower alkylthio groups herein indicate alkylamino and alkylthio groups containing a straight chain or branched alkyl group having about 1 to 4 carbon atoms. The lower alkylamino groups include, for example, methylamino, ethylamino, propylamino and t-butylamino groups. The lower alkylthio groups include, for example, methylthio, ethylthio, propylthio and butylthio groups.

The compounds of the formula (I) have the following tautomerism in the thiadiazole moiety in the structural formula and the tautomers are also included in the present invention as a matter of course:

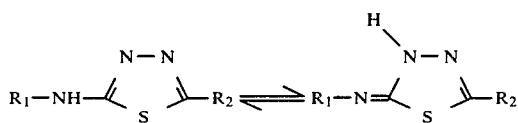

Now, the description will be made on the process for the production of the 1,3,4-thiadiazole derivatives of the present invention.

A typical process for producing the compounds of the present invention may be represented by the following chemical formula:

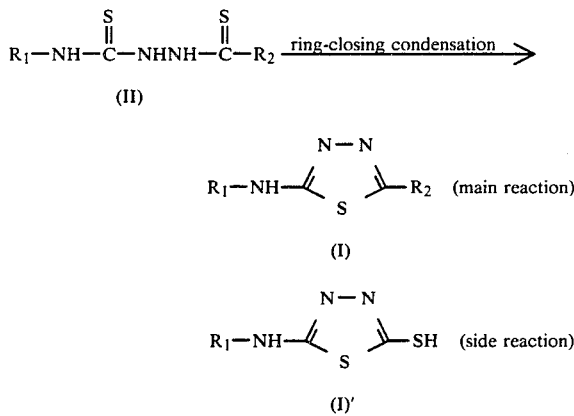

wherein $R_1$ and $R_2$ have the same meaning as above.

As shown by the above reaction formula, the compounds (I) of the present invention can be produced by ring-closing condensation of starting bithioureas or thiocarbamyl dithiocarbazinic acid esters of the general formula (II):

When the above-mentioned ring-closing condensation reaction is carried out in an aqueous solution of an inorganic acid or organic acid, side reactions occur easily in addition to the main reaction of the above formula. It has been found, however, that when the ring-closing reaction is carried out in an organic solvent preferably in the presence of a condensing agent, substantially only the main reaction occurs.

The organic solvents usable in the above-mentioned reaction include, for example, ethanol, n-propanol, benzene, toluene, tetrahydrofuran (hereinafter referred to as THF), 1,4-dioxane, pyridine, and dimethylformamide (hereinafter referred to as DMF).

The condensing agents include, for example, N,N'-dicyclohexylcarbodiimide (hereinafter referred to as DCC), N,N'-carbonyldiimidazole (hereinafter referred to as CDI), diethyl azodicarboxylate/triphenylphosphine and 2,2'-dipyridyl disulfide/triphenylphosphine. Among them, DCC is particularly preferred.

The condensing agent is used in an amount of generally 1 to 3 mols per mol of the compound of the formula (II).

The reaction conditions vary depending on the variety of the solvent. Generally, the reaction is carried out preferably at a temperature ranging from room temperature to reflux temperature for 1 to 40 h.

As described above, the compounds (I) of the present invention may be produced by a ring-closing condensation of the starting compound (II) in an organic solvent preferably in the presence of a condensing agent (see Examples 1, 3, 4 and 5).

Generally, the starting compound of the formula (II) is prepared previously. In some cases, however, the intended compound may be prepared directly by the following series of the reactions including the reaction for the preparation of the starting compound (see Example 6):

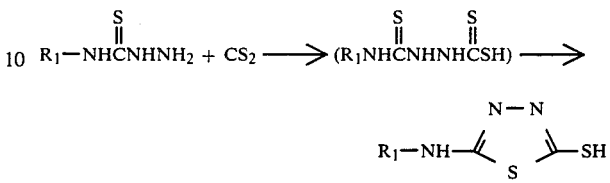

An intended compound (I)' in which $R_2$ represents —SH group can be obtained from another starting compound of the formula (II) which contains an easily removable group particularly phenylamino group, in place of the substituent $R_2$ by the ring-closing condensation in an aqueous acid solution in such a manner that the side-reaction is effected preferentially (see Example 2).

The thus obtained compound (I) of the present invention is a new compound having an excellent antagonism to histamine $H_2$ receptors and useful as a long lasting inhibitor to secretion of acid in the stomach or antiulcer agent.

The antiulcer agent of the present invention contains the compound of the above formula (I) or its acid addition salt as the effective ingredient.

The acid-addition salt may be prepared by an ordinary process.

The suitable acids for use in the preparation of the acid-addition salts include, for example, hydrochloric acid, hydrobromic acid, phosphoric acid, acetic acid, maleic acid, fumaric acid, lactic acid, tartaric acid, citric acid and gluconic acid.

The antiulcer agent of the present invention may be administered either perorally or parenterally.

When the antiulcer agent is administered perorally, it is formulated generally into tablets, powders, capsules, granules or syrups. When the antiulcer agent is administered parenterally, it is formulated into injections or suppositories.

In both cases, the effective ingredient may be mixed with known excipients and adjuvants used generally for the formulation of the preparations such as polyvinyl pyrrolidone, sodium chondroitin sulfate, gelatin, human serum albumin, dextran T-10, calcium gluconate, calcium pantothenate, calcium lactate, β-cyclodextrin, lactose, starch, magnesium stearate, talc, vegetable oil, carboxymethylcellulose, citric acid, sodium dihydrogenphosphate, mannitol, crystalline cellulose and polyvinyl alcohol to obtain products of various forms.

The effective dose of the antiulcer agent of the present invention is generally 0.1 to 100 mg/kg. The dose should be determined by taking various factors, such as the symptoms and age of the patient, administration method, form of the agent and number of times of the administration, into account.

The compound (I) of the present invention has only a low toxicity allowable as a medicine.

For example, the acute toxicities of a compound of the formula (I) wherein $R_2$ represents —$NH_2$ in mice and rats are as shown in Table 1. The acute toxicities of compounds of the formula (I) wherein $R_2$ represents —NHCH$_3$, —SH or —SCH$_3$ are nearly equal to that shown in Table 1.

TABLE 1

| LD$_{50}$ (mg/kg) | Peroral | Intravenous injection |
|---|---|---|
| Mice | 1220 | 53.2 |
| Rats | 1410 | 91.6 |

Process for producing the compounds of the present invention will be illustrated below. In the following referential examples, processes for producing the starting materials will be shown.

REFERENTIAL EXAMPLE 1

N-3-[3-(1-piperidinomethyl)phenoxy]propyl-N'-methylbithiourea 2.03 g of N-3-[3-(1-piperidinomethyl)phenoxy]propyl isothiocyanate and 0.74 g of 4-methyl-3-thiosemicarbazide were stirred in 20 ml of ethanol at room temperature for 3 days. The reaction liquid was concentrated to dryness under reduced pressure. Ethyl ether was added to the residue. After filtration, 2.06 g of the intended compound was obtained.

REFERENTIAL EXAMPLE 2

N-3-[3-(1-piperidinomethyl)phenoxy]propyl-N'-phenylbithiourea 2.03 g of N-3-[3-(1-piperidinomethyl)phenoxy]propyl isothiocyanate and 1.17 g of 4-phenyl-3-thiosemicarbazide were added to 20 ml of ethanol and the mixture was stirred at 50° C. for 18 h and concentrated to dryness under reduced pressure. The residue was purified according to a silica gel column chromatography using chloroform containing 3% of methanol as an eluent to obtain 2.00 g of the intended compound.

REFERENTIAL EXAMPLE 3

Methyl N-3-[3-(1-piperidinomethyl)phenoxy]propyl-thiocarbamyl dithiocarbadinate 450 mg of N-3-[3-(1-piperidinomethyl)phenoxy]propyl isothiocyanate and 189 mg of methyl dithiocarbadinate were added to 5 ml of THF. The mixture was stirred at room temperature for 20 h. The resulting solution was concentrated to dryness under reduced pressure. A liquid mixture of chloroform and ethyl ether (1:1) was added to the residue. After a filtration, 592 mg of the intended compound was obtained.

The following production examples will illustrate the process for producing the compounds of the present invention by the ring-closing condensation of the starting compounds.

PRODUCTION EXAMPLE 1

2-N-{3-[3-(1-piperidinomethyl)phenoxy]propyl}amino-5-methylamino-1,3,4-thiadiazole 5 ml of THF was added to 396 mg of N-3-[3-(1-piperidinomethyl)phenoxy]propyl-N'-methylbithiourea and 248 mg of DCC. The mixture was stirred at room temperature for 18 h and then under reflux for 3.5 h. The reaction liquid was cooled to room temperature. After concentration, the residue was dissolved in chloroform. 10% aqueous solution of acetic acid was added to the solution and the mixture was stirred at room temperature for 15 min. The reaction liquid was made basic with 3% aqueous potassium carbonate solution. After an extraction with chloroform, an organic layer was dried over anhydrous sodium carbonate and then concentrated. A small amount of chloroform was added to the residue and an insoluble matter was filtered out. After purification according to a column chromatography using silica gel as the carrier and a mixture of chloroform and ethanol (19:1) as the eluent, 270 mg of the intended compound was obtained. Yield: 74.7%.

NMR (CDCl$_3$): δ: 1.10–1.80 (6H, m); 1.90–2.63 (6H, m); 2.93 (3H, s); 3.26–3.73 (4H, m); 4.02 (2H, t, J=6 Hz); 4.70–6.20 (2H, s, disappeared with heavy water).

$^{13}$C NMR (DMSO-d$_6$): δ: 23.895 (t), 25.421 (t); 28.415 (t), 30.646 (q); 40.980 (t), 53.778 (t); 62.644 (t), 64.875 (t); 112.663 (d), 114.659 (d); 120.826 (d), 128.928 (d); 139.904 (s), 158.453 (s); 159.457 (s), 160.331 (s).

MS m/z 361M$^+$.

The same procedure as in Production Example 1 was repeated except that THF used as the reaction solvent was replaced with 1,4-dioxane or pyridine or DCC (condensing agent) was not used. Yields of the products are shown in Table 1.

TABLE 1

| Condensing agent | Solvent | Yield (%) |
|---|---|---|
| DCC | THF | 75 |
| DCC | 1,4-dioxane | 68 |
| DCC | pyridine | 38 |
| none | THF | 48 |

PRODUCTION EXAMPLE 2

200 mg of N-3-[3-(1-piperidinomethyl)phenoxy]propyl-N'-phenylbithiourea obtained in Referential Example 2 was added to 10 ml of 2N-hydrochloric acid. The mixture was stirred under heating to 100° to 105° C. for 1 h and then concentrated to dryness under reduced pressure. Water was added to a thick syrup-like residue to obtain a solution. Potassium carbonate was added to the solution under cooling with ice to adjust the solution to pH 9. After extraction with ethyl acetate, the extract was dried over magnesium sulfate and then concentrated to dryness under reduced pressure to obtain a thick syrup-like product. The product was purified according to a silica gel column chromatography using chloroform containing 5% of methanol as the eluent to obtain 118 mg (yield: 74.2%) of 2-N-{3-[3-(1-piperidinomethyl)phenoxy]propyl}amino-5-mercapto-1,3,4-thiadiazole.

NMR (CDCl$_3$): δ: 1.10–1.76 (6H, m); 1.97 (2H, t, J=6 Hz); 2.20–2.73 (4H, m); 3.10–3.65 (4H, m); 4.00 (2H, t, J=6 Hz); 6.66–7.57 (4H, m).

MS m/z 364 (M+).

PRODUCTION EXAMPLE 3

490 mg of methyl N-3-[3-(1-piperidinomethyl)-phenoxy]-propyl-thiocarbamyldithiocarbadinate obtained in Referential Example 3 was added to 15 ml of n-propanol. The mixture was stirred under heating and reflux for about 6 h. The reaction liquid was concentrated to dryness under reduced pressure. A thick syrup-like residue was purified according to a silica gel column chromatography using chloroform containing 4% of methanol as the eluent. After recrystallization from benzene/hexane, 342 mg (yield: 75.3%) of 2-N-{3-[3-(1-piperidinomethyl)phenoxy]propyl}amino-5-methylthio-1,3,4-thiadiazole was obtained in the form of colorless, needle-like crystals. m.p. 106°–107.5° C.

NMR (CDCl$_3$): δ: 1.25–1.90 (6H, m); 2.16 (2H, t, J=6 Hz); 2.33–2.80 (7H, m); 3.35–3.80 (4H, m); 4.15 (2H, t, J=6 Hz); 6.10–6.70 (1H, s, broad; disappeared when heavy water was added); 6.70–7.50 (4H, m);

MS m/z 378 (M+).

PRODUCTION EXAMPLE 4

6 ml of THF was added to 610 mg of N-3-[3-(1-piperidinomethyl)phenoxy]propylbithiourea and 330 mg of DCC. The resulting solution was stirred at room temperature for 21 h and the reaction was carried out under reflux for 2.5 h. The reaction liquid was left to cool to room temperature and concentrated under reduced pressure. The residue was dissolved in chloroform and washed with 5% acetic acid, aqueous potassium carbonate solution and water successively. The chloroform layer was dried over anhydrous sodium sulfate. The chloroform layer was separated out. Chloroform was evaporated off. Acetonitrile was added to the resulting thick syrup-like residue and crystals thus formed were filtered out to obtain 305 mg (yield: 54.9%) of 2-N-{3-[3-(1-piperidinomethyl)phenoxy]propyl}amino-5-amino-1,3,4-thiadiazole.

Melting point: 162°–165°C.

NMR (DMSO-d$_6$): δ: 1.10–1.69 (6H, m); 1.79–2.53 (6H, m); 3.00–3.63 (4H, m); 4.06 (2H, t, J=6 Hz); 6.01–6.52 (2H, s, disappeared with heavy water); 6.70–7.50 (5H, m, 1H disappeared with heavy water).

MS m/z 347 (M+).

PRODUCTION EXAMPLE 5

1.2 g of N-3-[3-(1-piperidinomethyl)phenoxy]propylbithiourea and 500 mg of CDI were reacted together in 20 ml of THF under stirring under heating to 50° C. for 10 h.

The reaction liquid was concentrated under reduced pressure. The residue was dissolved in chloroform. The resulting solution was washed with 5% acetic acid, 5% aqueous potassium carbonate solution and water successively. The chloroform layer was dried over anhydrous sodium sulfate. Chloroform was distilled off and the residue was dissolved in ethanol saturated with hydrogen chloride gas. The solution was left to stand for a while and the solvent was then evaporated off. The residue was dissolved in anhydrous methanol. Ethyl acetate was added to the solution and crystals thus formed were filtered out to obtain 1.0 g (yield: 82.7%) of 2-N-{3-[3-(1-piperidinomethyl)phenoxy]propyl}amino-5-amino-1,3,4-thiadiazole hydrochloride.

Melting point: 215.5°–216.5° C. (recrystallized from water).

NMR (DMSO-d$_6$): δ: 1.61–2.33 (8H, m) 2.73–3.60 (6H, m) 3.83–4.37 (4H, m) 5.70–7.65 (8H, m, 4H disappeared when heavy water was added).

| Elementary analysis for C$_{17}$H$_{25}$N$_5$OS.HCl: | | | |
|---|---|---|---|
| | C (%) | H (%) | N (%) |
| Calculated: | 53.19 | 6.83 | 18.24 |
| Found: | 53.25 | 6.98 | 18.01 |

EXAMPLE 6

645 mg of 4-{3-[3-(1-piperidinomethyl)phenoxy]propyl}-3-thiosemicarbazide was dissolved in 10 ml of DMF. 190 mg of carbon disulfide diluted with 10 ml of ethanol was added dropwise thereto under stirring. Then, the stirring was continued for 1 h and the mixture was heated under reflux for 3.5 h.

After completion of the reaction, the solvent was distilled off and the residue was purified according to a column chromatography using silica gel as the carrier and a mixture of ethanol and chloroform (1:19 v/v) as the eluent to obtain 480 mg (yield: 65.8%) of 2-N-{3-[3-(1-piperidinomethyl)phenoxy]propyl}amino-5-mercapto-1,3,4-thiadiazole.

The results of NMR and Mass spectrometry of the compound coincided with those of the compound obtained in Example 2.

EXAMPLE 7

The same procedure as in Example 1 was repeated except that the starting compound (II) was altered to obtain the following compounds:

| Compound of formula (I) | R$_2$— | Yield (%) |
|---|---|---|
| A | —NHC$_2$H$_5$ | 64 |
| B | —NHC(CH$_3$)$_3$ | 56 |
| C | —NH—⟨phenyl⟩ | 41 |
| D | —NHCO—⟨phenyl⟩ | 47 |

The physicochemical properties of the compounds were as follows:

Compound A

NMR (CDCl$_3$): δ: 1.0–1.8 (9H, m); 2.0–2.7 (6H, m); 3.0–3.7 (6H, m); 4.07 (2H, t, J=6 Hz); 6.0–6.6 (2H, s, disappeared with heavy water); 6.7–7.5 (4H, m).

Mass M+ 375.

Compound B

NMR (CDCl$_3$): δ: 1.1–2.7 (21H, m); 3.3–3.7 (4H, m); 4.07 (2H, t, J=6 Hz); 4.7–5.1 (1H, s, disappeared with heavy water); 5.8–6.9 (1H, s, disappeared with heavy water); 6.6–7.4 (4H, m).

Mass M+ 403.

Compound C

NMR (CDCl$_3$): δ: 0.8–2.6 (22H, m); 2.9–3.7 (4H, m); 4.07 (2H, t, J=6 Hz); 5.2–6.3 (2H, s, disappeared with heavy water); 6.6–7.5 (4H, m).

Mass M+ 429.

Compound D

NMR (CDCl$_3$): δ: 1.1–3.1 (12H, m); 3.3–4.6 (6H, m); 6.2–8.6 (10H, m); 9.7–10.5 (2H, s, disappeared with heavy water).

Mass M+ 451.

The excellent antagonism to histamine H$_2$ receptors, effect of inhibiting the secretion of acid in the stomach and antiulcer effect of the compounds of the present invention will be proved by the following tests:

TEST 1

Antagonism to histamine $H_2$ receptors

Heads of male Hartley guinea pigs weighing 300 to 350 g were hit. After bleeding, the heart was extracted. The atria were taken out in a Locke-Ringer's solution. Both ends of each atrium were fitted with a filament. The atrium was suspended under a tension of 500 mg by means of the filaments at both ends thereof in a 30 ml Magnus tube containing the Locke-Ringer's solution maintained at 37° C. in which a gaseous mixture of 95% of $O_2$ and 5% of $CO_2$ was introduced. The contraction action of the atrium was measured by means of a strain gauge (TB-612T; a product of Nihon Koden Co.) and the output was determined from a heart rate determined with a tachometer (AT-600 G; a product of Nihon Koden Co.).

Histamine (used in the form of its dihydrochloride; the same shall apply hereinafter) in a concentration of $1 \times 10^{-8}$M to $1 \times 10^{-4}$M was added to the Magnus tube cumulatively in such a dose that the distances between the logarithms of the amounts thereof added would be equal ($\frac{1}{2}$) until the maximum reaction of the heart rate increase was obtained. A curve showing the relationship between the dose of histamine and the reaction was thus obtained. The Magnus tube was washed several times and the atrium was stabilized for 30 min. Then, the above-mentioned process was repeated to obtain a curve showing the relationship between the dose of histamine and the reaction.

The Magnus tube was washed several times and the atrium was stabilized for 30 min. Then, a test compound was placed in the Magnus tube. After 10 min, a curve showing a relationship between the dose of histamine and the reaction in the presence of the test compound was obtained.

A $PA_2$ value of the test compound (negative number of logarithm of molar concentration of the test compound required for increasing the histamine concentration in the Magnus tube necessitated for causing a given reaction to 2-folds) was calculated from the second histamine dose/reaction curve and the third histamine dose/reaction curve obtained in the presence of the test compound by J. M. Van Rossum's method [Arch. int. Pharmacodyn., 143, 299 (1963)].

The results are shown in Table 2.

TABLE 2

| | Test Compound | $PA_2$ value |
|---|---|---|
| Present invention | $H_2$—33 | 6.60 |
| | $H_2$—37 | 6.50 |
| | $H_2$—41 | 7.02 |
| | TAS | 7.10 |
| Comparative | cimetidine | 6.00 |

TABLE 2-continued

| Test Compound | $PA_2$ value |
|---|---|
| ranitidine | 6.51 |

In the table and the following tests, symbols $H_2$-33, $H_2$-37, $H_2$-41 and TAS indicate the following compounds:

$H_2$-33: 2-N-{3-[3-(1-piperidinomethyl)phenoxy]-propyl}amino-5-methylamino-1,3,4-thiadiazole, $H_2$-37: 2-N-{3-(1-piperidinomethyl)phenoxy]propyl}amino-5-mercapto-1,3,4-thiadiazole, $H_2$-41: 2-N-{3-[3-(1-piperidinomethyl)phenoxy]propyl}-amino-5-methylthio-1,3,4-thiadiazole, and TAS: 2-N-{3-[3-(1-piperidinomethyl)phenoxy]propyl}-amino-5-amino-1,3,4-thiadiazole hydrochloride.

TEST 2

Effects of inhibition of the secretion of acid in the stomach

Donryu male rats weighing 210 to 230 g after fasting for 48 h were subjected to an abdominal operation under etheral anesthesia. The pylorus was ligated. Immediately thereafter, a test sample was placed in the duodenum and the abdomen was closed.

Six hour after the administration of the test sample, the stomach was taken out under etheral anesthesia and the gastric juice was taken out.

The gastric juice was centrifuged. The quantity, acidity and pepsin activity of the supernatant liquid were determined.

The acidity was determined by titration with 0.1N NaOH till pH 7.0 by means of a buret. The amount of the acid discharged per hour was calculated by multiplying the acidity by the quantity of the juice.

Pepsin activity was determined by Anson's method [J. gen. Physiol. 21 79 (1938)].

In the tests of $H_2$-33 and $H_2$-37 (compounds of the present invention), cimetidine was used as a comparative medicine. In the test of TAS, cimetidine and ranitidine were used as comparative medicines. The tests were effected using three standard doses of 6.7 mg/kg, 20 mg/kg and 60 mg/kg.

The test results of $H_2$-33 are shown in Table 3. Those of $H_2$-37 are shown in Table 4 and those of TAS are shown in Table 5.

The results of the tests of $H_2$-33 and $H_2$-37 are the averages of respective groups consisting of five rats. The results of the tests of TAS are the averages of the group consisting of ten rats.

The test results of TAS in doses of as small as 0.7 mg/kg, 2.2 mg/kg, 6.7 mg/kg and 20 mg/kg are shown in Table 6.

TABLE 3

| Test Compound | $H_2$—33 (present invention) | | | Cimetidine (comparative) | | | (control) |
|---|---|---|---|---|---|---|---|
| Dose (mg/kg) | 6.7 | 20.0 | 60.0 | 6.7 | 20.0 | 60.0 | |
| Gastric juice secreted (ml) | 4.8 | 2.5 | 2.9 | 5.4 | 4.8 | 3.7 | 5.8 |
| Inhibition rate (%) | 17.0 | 57.0 | 50.0 | 6.9 | 17.0 | 36.0 | 0 |
| Acidity (meq $H^+$/l) | 70.0 | 52.0 | 24.0 | 85.0 | 77.0 | 61.0 | 81.0 |
| Inhibition rate (%) | 14.0 | 36.0 | 70.0 | −5.0 | 5.4 | 25.0 | 0 |
| Amount of acid discharged ($\mu$Eq/H) | 54.0 | 25.0 | 10.0 | 79.0 | 57.0 | 38.0 | 83.0 |
| Inhibition rate (%) | 35.0 | 70.0 | 88.0 | 5.3 | 31.0 | 55.0 | 0 |
| Pepsin activity (mg/ml) | 6.4 | 6.2 | 4.9 | 7.0 | 6.2 | 6.3 | 6.2 |

TABLE 3-continued

| Test Compound | H₂—33 (present invention) | | | Cimetidine (comparative) | | | (control) |
|---|---|---|---|---|---|---|---|
| Inhibition rate (%) | −3.2 | 0 | 21.0 | −13.0 | 0 | −1.6 | 0 |

TABLE 4

| Test Compound | H₂—37 (present invention) | | | Cimetidine (comparative) | | | 0.5% CMC-Na (control) |
|---|---|---|---|---|---|---|---|
| Dose (mg/kg) | 6.7 | 20.0 | 60.0 | 6.7 | 20.0 | 60.0 | |
| Gastric juice secreted (ml) | 4.6 | 5.2 | 3.6 | 5.0 | 4.5 | 4.5 | 6.3 |
| Inhibition rate (%) | 27.0 | 18.0 | 43.0 | 21.0 | 29.0 | 29.0 | 0 |
| Acidity (meq H⁺/l) | 85.0 | 81.0 | 67.0 | 76.0 | 79.0 | 62.0 | 89.0 |
| Inhibition rate (%) | 4.5 | 9.0 | 24.0 | 15.0 | 11.0 | 31.0 | 0 |
| Amount of acid discharged (μEq/h) | 67.0 | 68.0 | 37.0 | 67.0 | 61.0 | 47.0 | 86.0 |
| Inhibition rate (%) | 22.0 | 21.0 | 57.0 | 22.0 | 29.0 | 45.0 | 0 |
| Pepsin activity (mg/ml) | 5.9 | 5.9 | 5.4 | 5.5 | 5.1 | 6.3 | 5.5 |
| Inhibition rate (%) | −7.3 | −7.3 | 1.8 | 0 | 7.3 | −15.0 | 0 |

TABLE 5

| Test Compound | TAS (present invention) | | | Cimetidine (comparative) | | | Ranitidine (comparative) | | |
|---|---|---|---|---|---|---|---|---|---|
| Dose (mg/kg) | 6.7 | 20.0 | 60.0 | 6.7 | 20.0 | 60.0 | 6.7 | 20.0 | 60.0 |
| Rate of inhibition of the secretion of gastric juice (%) | 57.7 | 65.4 | 82.7 | 3.8 | 7.7 | 28.8 | 7.7 | 23.1 | 34.6 |
| Rate of inhibition of acidity (%) | 67.4 | 74.0 | 100 | 2.9 | 12.4 | 30.9 | 11.3 | 28.2 | 50.1 |
| Rate of control of the amount of acid discharged (%) | 85.7 | 91.4 | 100 | 2.5 | 25.6 | 51.1 | 19.3 | 54.2 | 67.4 |
| Rate of control of the amount of pepsin discharged (%) | 13.6 | 25.8 | 86.4 | −6.1 | 6.1 | 4.5 | 1.5 | −4.5 | −3.0 |

TABLE 6

| Test Compound | TAS (present invention) | | | |
|---|---|---|---|---|
| Dose (mg/kg) | 0.7 | 2.2 | 6.7 | 20.0 |
| Rate of inhibition of the secretion of gastric juice (%) | 23.51 | 43.1 | 52.9 | 66.7 |
| Rate of inhibition of acidity (%) | 22.4 | 40.9 | 65.7 | 75.0 |
| Rate of control of the amount of acid discharged (%) | 40.2 | 63.5 | 81.5 | 91.5 |
| Rate of control of the amount of pepsin discharged (%) | −1.3 | 5.1 | 15.2 | 30.4 |

TEST 3

Antiulcer effects

Donryu rats weighing 200 to 230 g were used. Each group consisted of 6 rats. After fasting for 72 h, the rats were subjected to an abdominal operation under etheral anesthesia. The pylorus was ligated. Immediately thereafter, a given dose of a test sample was placed in the duodenum. Thereafter, neither food nor water was given. After 8 h, the stomach was taken out under etheral anesthesia and immersed in 1% formalin solution for 10 min. The stomach was cut along the greater curvature. The area of ulcer formed in the forestomach was determined by an anatomico-microscopic observation (magnification: ×10). The rate of control of the ulcer (%) was calculated as compared with a control.

This test was effected according to the specification of Gastroenterology 4, (5), 43–61 (1945).

The test results are shown in Table 5. With 12.5 to 50 mg/kg of TAS, antiulcer effects far superior to those obtained by using 200 mg/kg of cimetidine or ranitidine were obtained.

TABLE 7

| Test sample | Present invention TAS | | | | Comparative | | | |
|---|---|---|---|---|---|---|---|---|
| | | | | | Cimetidine | | Ranitidine | |
| Dose (mg/kg) | 6.3 | 12.5 | 25.0 | 50.0 | 100 | 200 | 100 | 200 |
| Inhibition rate (%) | 60.0 | 90.0 | 95.0 | 100 | 10 | 60 | 50 | 85 |

What is claimed is:

1. A 1,3,4-Thiadiazole compound having the general formula:

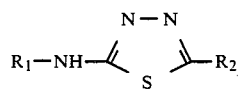

wherein R₁ comprises a 1-(3-piperidinomethyl)phenoxypropyl substituent having the formula:

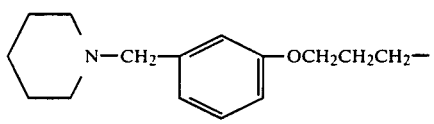

and $R_2$ represents an amino, lower alkylamino, cyclohexylamino, benzolylamino, mercapto, or lower alkylthio group and and the acid-addition salts thereof selected from the group consisting of hydrochloric, hydrobromic, phosphoric, acetic, maleic, fumaric, lactic, tartaric, citric and gluconic acid salts.

2. A compounds according to claim 1 wherein $R_2$ represents an amino group.

3. An antiulcer agent, comprising:
a 1,3,4-thiadiazole compound, as an active ingredient, having the general formula:

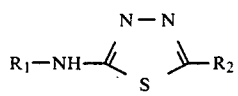

wherein $R_1$ comprises a 1-(3-piperidinomethyl)-phenoxypropyl substituent having the formula:

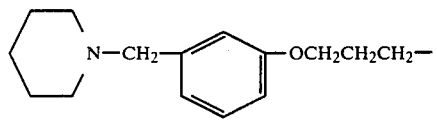

and $R_2$ represents an amino, lower alkylamino, cyclohexylamino, benzolylamino, mercapto, or lower alkylthio group and the acid-addition salts thereof selected from the group consisting of hydrochloric, hydrobromic, phosphoric, acetic, maleic, fumaric, lactic, tartaric, citric and gluconic acid salts; and an excipient or adjuvant, in any amount sufficient to prepare a peroral or parenteral formulation, selected from the group consisting of polyvinyl pyrrolidone, sodium chondroitin sulfate, gelatin, human serum albumin, dextran T-10, calcium gluconate, calcium pantothenate, calcium lactate, β-cyclodextrin, lactose, starch, magnesium stearate, talc, vegetable oil, carboxymethylcellulose, citric acid, sodium dihydrogenphosphate, mannitol, crystalline cellulose and polyvinyl alcohol.

4. An antiulcer agent according to claim 3 wherein $R_2$ represents an amino group.

5. A process for producing a 1,3,4-thiadiazole compound having the general formula:

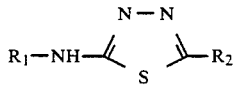

wherein $R_1$ comprises a 1-(3-piperidinomethyl)phenoxypropyl substituent having the formula:

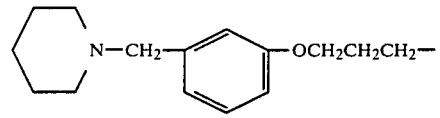

and $R_2$ represents an amino, lower alkylamino, cyclohexylamino, benzolylamino, mercapto, or lower alkylthio group and the acid-addition salts thereof selected from the group consisting of hydrochloric, hydrobromic, phosphoric, acetic, maleic, fumaric, lactic, tartaric, citric and gluconic acid salts, comprising the steps of:
providing at least one bithiourea or thiocarbamyl dithiocarbazinate compound of the general formula:

wherein $R_1$ comprises a 1-(3-piperidinomethyl)-phenoxypropyl substituent having the formula:

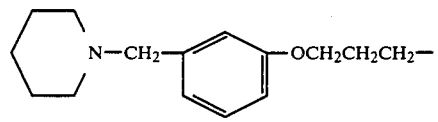

and $R_2$ represents an amino, lower alkylamino, cyclohexylamino, benzoylamino, mercapto, or lower alkylthio group and the acid-addition salts thereof selected from the group consisting of hydrochloric, hydrobromic, phosphoric, acetic, maleic, fumaric, lactic, tartaric, citric and gluconic acid salts;

reacting said bithioureas or thiocarbamyl dithiocarbazinate with an aqueous solution of an organic solvent; and purifying said 1,3,4-thiadiazole compound from said aqueous solution of organic solvent.

6. The process according to claim 5, wherein said reacting step further comprises the step of reacting said bithioureas or thiocarbamyl dithiocarbazinate with an aqueous solution of an organic solvent in the presence of a condensing agent.

7. The process according to claim 5, wherein said organic solvent is selected from the group consisting of ethanol, n-propanol, benzene, toluene, tetrahydrofuran, 1,4-dioxane, pyridine and dimethylformamide.

8. The process according to claim 5, wherein said purifying step further comprises column chromatography with an eluent comprising chloroform and an organic alcohol selected from the group consisting of methanol and ethanol.

9. The process according to claim 5, wherein said purifying step further comprises filtration.

10. The process according to claim 6, wherein said condensing agent is selected from the group consisting of N,N'-dicyclohexylcarbodiimide, N,N'-carbonyldiimidazole, diethyl azodicarboxylate/triphenylphosphine and 2,2' dipyridyl disulfide/triphenylphosphine.

11. The process according to claim 5, wherein said condensing agent is present in an amount in the range of about 1 to 3 moles per mole of bithiourea or thiocarbamyl dithiocarbazinate used.

12. The process according to claim 5, wherein said reacting step is carried out at a temperature in the range of about room temperature to reflux temperature and for a time period in the range of about 1 to 40 hours.

* * * * *

UNITED STATES PATENT AND TRADEMARK OFFICE
CERTIFICATE OF CORRECTION

PATENT NO. : 4,587,254
DATED : May 6, 1986
INVENTOR(S) : Hatsunori Toyofuku et al.

It is certified that error appears in the above-identified patent and that said Letters Patent is hereby corrected as shown below:

Column 10, line 11, delete "{3-(" and insert therefor -- {3-[3-( --.

Claim 2, line 1, delete "compounds" and insert therefor -- compound --.

Signed and Sealed this

Fifteenth Day of July 1986

[SEAL]

Attest:

DONALD J. QUIGG

Attesting Officer

Commissioner of Patents and Trademarks